United States Patent
Zhou et al.

(10) Patent No.: US 12,172,034 B2
(45) Date of Patent: Dec. 24, 2024

(54) METHOD AND APPARATUS FOR CONTROLLING MULTILEAF COLLIMATOR IN RADIOTHERAPY

(71) Applicant: MANTEIA TECHNOLOGIES CO., LTD., Fujian (CN)

(72) Inventors: Qichao Zhou, Fujian (CN); Wei Zhang, Fujian (CN); Lingke Kong, Fujian (CN); Liwan Shi, Fujian (CN); Qin Lin, Fujian (CN)

(73) Assignee: MANTEIA TECHNOLOGIES CO., LTD., Fujian (CN)

( * ) Notice: Subject to any disclaimer, the term of this patent is extended or adjusted under 35 U.S.C. 154(b) by 17 days.

(21) Appl. No.: 17/620,133

(22) PCT Filed: Nov. 26, 2020

(86) PCT No.: PCT/CN2020/131876
§ 371 (c)(1),
(2) Date: Dec. 17, 2021

(87) PCT Pub. No.: WO2022/088341
PCT Pub. Date: May 5, 2022

(65) Prior Publication Data
US 2023/0264048 A1    Aug. 24, 2023

(30) Foreign Application Priority Data
Oct. 30, 2020   (CN) .......................... 202011194094.2

(51) Int. Cl.
*A61N 5/10*     (2006.01)
(52) U.S. Cl.
CPC ........... *A61N 5/1065* (2013.01); *A61N 5/103* (2013.01); *A61N 5/1045* (2013.01)

(58) Field of Classification Search
CPC .... A61N 5/1065; A61N 5/103; A61N 5/1045; A61N 5/1036; A61N 5/1048
See application file for complete search history.

(56) References Cited

U.S. PATENT DOCUMENTS

| | | | |
|---|---|---|---|
| 5,647,663 A | * | 7/1997 | Holmes ................... G16Z 99/00 600/407 |
| 7,469,035 B2 | | 12/2008 | Keall et al. |
| (Continued) | | | |

FOREIGN PATENT DOCUMENTS

| | | |
|---|---|---|
| CN | 101247852 A | 8/2008 |
| CN | 103127623 A | 6/2013 |
| (Continued) | | |

OTHER PUBLICATIONS

International Search Report for corresponding application PCT/CN2020/131876 filed Nov. 26, 2020; Mail date Jul. 22, 2021.

(Continued)

*Primary Examiner* — Courtney D Thomas
(74) *Attorney, Agent, or Firm* — Samson G. Yu

(57) ABSTRACT

Disclosed are a method and an apparatus for controlling multileaf collimator in radiotherapy. The method comprises: acquiring a preset model; outputting, regarding a radiotherapy target, a target leaf sequence of a multileaf collimator through the preset model, to obtain a planning file; and importing the planning file into a radiotherapy planning system to control a linear accelerator to operate, so as to implement a radiotherapy plan, which solves the technical problem in the related art of poor accuracy and stability in determining a leaf sequence of a multileaf collimator.

8 Claims, 1 Drawing Sheet

(56) References Cited

U.S. PATENT DOCUMENTS

| | | |
|---|---|---|
| 2012/0065489 A1 | 3/2012 | Nord et al. |
| 2018/0154183 A1 | 6/2018 | Sahadevan |
| 2019/0030370 A1 | 1/2019 | Hibbard et al. |
| 2020/0254277 A1 | 8/2020 | Eriksson et al. |

FOREIGN PATENT DOCUMENTS

| | | |
|---|---|---|
| CN | 104117151 A | 10/2014 |
| CN | 107349531 A | 11/2017 |
| CN | 107582030 A | 1/2018 |
| CN | 107715314 A | 2/2018 |
| CN | 109031440 A | 12/2018 |
| CN | 109496160 A | 3/2019 |
| CN | 109621231 A | 4/2019 |
| CN | 109771842 A | 5/2019 |
| CN | 109843377 A | 6/2019 |
| CN | 109920512 A | 6/2019 |
| CN | 109979564 A | 7/2019 |
| CN | 110124214 A | 8/2019 |
| CN | 110944717 A | 3/2020 |
| CN | 111374690 A | 7/2020 |
| CN | 111417435 A | 7/2020 |
| CN | 111432879 A | 7/2020 |
| CN | 111589000 A | 8/2020 |
| CN | 111833988 A | 10/2020 |
| EP | 3590577 A1 | 1/2020 |
| WO | 2016160932 A1 | 10/2016 |
| WO | 2020064715 A1 | 4/2020 |

OTHER PUBLICATIONS

First search report of corresponding CN application No. 202011194094.2.

Second search report of corresponding CN application No. 202011194094.2.

* cited by examiner

METHOD AND APPARATUS FOR CONTROLLING MULTILEAF COLLIMATOR IN RADIOTHERAPY

CROSS-REFERENCE TO RELATED APPLICATION

The present disclosure claims priority to Chinese Patent Application No. 202011194094.2, filed to the China National Intellectual Property Administration on Oct. 30, 2020 and entitled "Method and Apparatus for Controlling Multileaf Collimator in Radiotherapy", which is incorporated herein by reference in its entirety.

TECHNICAL FIELD

The present disclosure relates to the technical field of radiotherapy control, and in particular, to a method and an apparatus for controlling multileaf collimator in radiotherapy.

BACKGROUND

The primary objective of radiotherapy is to reduce radiation to healthy tissues as much as possible while giving sufficient irradiation to a tumor target region. Beam conformation of a linear accelerator is an important method by which the radiation dose absorbed by healthy organs and tissues can be reduced to the greatest extent. A multileaf collimator is an important apparatus for implementing the method, and is a device fixed on a linear accelerator. The multileaf collimator is composed of a plurality of independently movable leaves, and these leaves are usually made of materials with a high atomic number, and can block some radiation beams to change the shape thereof, and also change the intensity thereof.

The multileaf collimator plays an important role in radiotherapy. It is a key module in intensity-modulated radiotherapy, and the intensity-modulated radiotherapy is one of the most important developments in oncology. In radiotherapy, radiation dose is arranged to be confined within a target volume as much as possible, and to be minimal within surrounding healthy tissues. The core technology to achieve this dose distribution is inverse planning, i.e., first providing a dose distribution required and then solving an integral equation to find an appropriate shape and intensity of beams. However, as the dose distribution required cannot be set directly, the integral equation cannot be solved directly according to the dose distribution. In most radiotherapy planning systems, two steps are usually taken to obtain the appropriate shape and intensity of beams, as well as an executable motion sequence of the multileaf collimator. In the first step, an objective function or a cost function is set and minimized to generate a beam intensity map, and this process is referred to as fluence map optimization. In the second step, a leaf sorting algorithm is applied to convert the intensity map into a set of executable shapes or motion trajectories of the multileaf collimator, and this process is further divided into two parts: firstly, according to the intensity map, calculation is performed to obtain an initial sequence, and then re-optimization is performed according to specific machine limitations of the linear accelerator to obtain a final leaf sequence of the multileaf collimator.

Although these two steps have been widely used in radiotherapy planning systems, they still have some limitations. The greatest limitation is derived from the leaf sorting algorithm. Currently, in the existing leaf sorting algorithms, optimization is basically performed by a mathematical method; however, a simulated leaf sequence of the multileaf collimator obtained through calculation according to these optimization methods usually needs to be re-optimized according to the machine limitations. This process will cause a certain loss of precision. In addition, a large radiation leakage dose will be brought to a patient and the treatment time will be prolonged when the machine performs treatment by a multileaf collimator having many excessive small shapes. On the other hand, when these algorithms are used to optimize an irradiation intensity, the precision is usually limited, and therefore it is difficult to achieve the optimal effect.

In view of the described problems, no effective solution has been proposed yet.

SUMMARY

Embodiments of the present disclosure provide a method and an apparatus for controlling multileaf collimator in radiotherapy, so as to at least solve the technical problem in the related art of poor accuracy and stability in determining a leaf sequence of a multileaf collimator.

According to one aspect of the embodiments of the present disclosure, a method for controlling multileaf collimator in radiotherapy is provided, comprising: acquiring a preset model; outputting, regarding a radiotherapy target, a target leaf sequence of a multileaf collimator through the preset model, to obtain a planning file; and importing the planning file into a radiotherapy planning system to control a linear accelerator to operate, so as to implement a radiotherapy plan.

Further, before acquiring a preset model, the method further comprises: acquiring sample data, wherein the sample data comprises: fluence maps in historical planning files; and performing reinforcement learning and training through a neural network model by using the sample data, to generate the preset model.

Further, before acquiring sample data, the method further comprises: setting environmental parameters of a training frame according to a model of the linear accelerator, wherein the environmental parameters at least comprise: a width of each leaf, a movement range of each leaf, a movement speed of each leaf, and a total number of leaves of the multileaf collimator; setting states of leaves of the training frame, wherein the states at least comprise: a leaf position where a current leaf is located, a currently obtained fluence map, and a target fluence map; and setting a reward function for the leaves of the training frame, wherein the reward function is used for calculating a difference between the currently outputted fluence map and the target fluence map, and allocating a reward corresponding to the leaf position.

Further, before acquiring sample data, the method further comprises: determining a simulated state of the multileaf collimator in an environment according to the environmental parameters, the states and the reward function.

Further, performing reinforcement learning and training through a neural network model by using the sample data to generate the preset model, comprises: performing reinforcement learning and training on the sample data and the simulated state of the multileaf collimator by a first network of the neural network model to obtain a simulated leaf sequence of the multileaf collimator, wherein the simulated leaf sequence of the multileaf collimator comprises: coordinate positions of the leaves and weights of irradiation fields; evaluating the simulated leaf sequence of the multileaf collimator by a second network in the neural network model; and adjusting parameters in the first network and the second network of the neural network model according to an evaluation result, to generate the preset model.

Further, after importing the planning file into a radiotherapy planning system to control a linear accelerator to operate so as to implement a radiotherapy plan, the method further comprises: importing the planning file into the radiotherapy planning system to control the linear accelerator to operate to acquire an actual fluence map; and evaluating the preset model based on the actual fluence map and the target fluence map.

According to another aspect of the embodiments of the present disclosure, an apparatus for controlling multileaf collimator in radiotherapy is further provided, wherein the apparatus comprises: a first acquisition unit, which is configured to acquire a preset model; a second acquisition unit, which is configured to output, regarding a radiotherapy target, a target leaf sequence of a multileaf collimator through the preset model to obtain a planning file; and a control unit, which is configured to import the planning file into a radiotherapy planning system to control a linear accelerator to operate, so as to implement a radiotherapy plan.

Further, the apparatus further comprises: a third acquisition unit, which is configured to acquire sample data before acquiring a preset model, wherein the sample data comprises: fluence maps in historical planning files; and a generation unit, which is configured to perform reinforcement learning and training through a neural network model by using the sample data to generate the preset model.

According to another aspect of the embodiments of the present disclosure, a non-transitory storage medium is further provided, the non-transitory storage medium comprises a program stored therein, wherein when the program runs, a device where the non-transitory storage medium is located is controlled to implement the method according to any one of the above.

According to another aspect of the embodiments of the present disclosure, an electronic apparatus is further provided, comprising a processor and a memory; computer-readable instructions are stored in the memory, and the processor is configured to run the computer-readable instructions, wherein when the computer-readable instructions are running, the method according to any one of the above is implemented.

In the embodiments of the present disclosure, by acquiring a preset model; outputting, regarding a radiotherapy target, a target leaf sequence of a multileaf collimator through the preset model, to obtain a planning file; and importing the planning file into a radiotherapy planning system to control a linear accelerator to operate, so as to implement a radiotherapy plan, the calculation and operation speed for calculating the leaf sequence of the multileaf collimator by using a pre-trained model is high, and the accuracy and stability of the leaf sequence can be improved, thereby shortening the treatment time of a patient, and also reducing the workload of physicists in designing a radiotherapy plan, which further solves the technical problem in the related art of poor accuracy and stability in determining a leaf sequence of a multileaf collimator.

BRIEF DESCRIPTION OF THE DRAWINGS

The drawings illustrated herein are used for providing further understanding of some embodiments of the present disclosure, constituting a part of some embodiments of the present disclosure; and illustrative embodiments of the present disclosure and illustrations thereof are used for explaining some embodiments of the present disclosure, rather than constituting inappropriate limitations on some embodiments of the present disclosure. In the drawings.

DETAILED DESCRIPTION OF THE EMBODIMENTS

Figure 1:
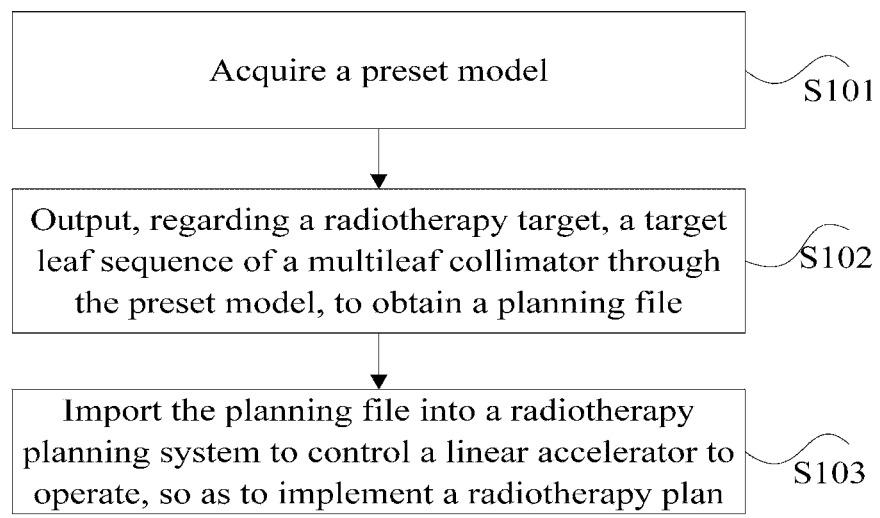
FIG. 1 is a flowchart of a method for controlling multileaf collimator in radiotherapy provided according to embodiments of the present disclosure.

In order to enable those skilled in the art to better understand the solutions of some embodiments of the present disclosure, hereinafter, the technical solutions in the embodiments of the present disclosure will be described clearly and thoroughly with reference to the accompanying drawings of embodiments of the present disclosure. Obviously, the embodiments as described are only some of the embodiments of the present disclosure, and are not all the embodiments. All other embodiments obtained by a person of ordinary skill in the art based on the embodiments of the present disclosure without any inventive effort shall all fall within the scope of protection of the present disclosure.

It should be noted that the terms "first", "second", etc., in the description, claims, and accompanying drawings of the present disclosure are used to distinguish similar objects, and are not necessarily used to describe a specific sequence or order. It should be understood that the data used may be interchanged where appropriate so that the embodiments of the present disclosure described herein can be implemented in sequences other than those illustrated or described herein. In addition, the terms "comprise" and "have", and any variations thereof are intended to cover a non-exclusive inclusion, for example, a process, method, system, product, or device that comprises a series of steps or units is not necessarily limited to those steps or units that are clearly listed, but may comprise other steps or units that are not clearly listed or inherent to such process, method, product, or device.

According to embodiments of the present disclosure, embodiments of a method for controlling multileaf collimator in radiotherapy are provided. It should be noted that the steps illustrated in the flowchart of the drawing can be executed in a computer system such as a set of computer-executable instructions, and although a logical order is shown in the flowchart, in some cases, the steps shown or described can be executed in a different order from that described here.

FIG. 1 is a flowchart of a method for controlling multileaf collimator in radiotherapy provided according to embodiments of the present disclosure. As shown in FIG. 1, the method comprises the following steps:

step S101, acquiring a preset model;

step S102, outputting, regarding a radiotherapy target, a target leaf sequence of a multileaf collimator through the preset model, to obtain a planning file, wherein the described planning file comprises a target leaf sequence of the multileaf collimator outputted by the preset model; and step S103: importing the planning file into a radiotherapy planning system to control a linear accelerator to operate, so as to implement a radiotherapy plan.

After importing the planning file comprising a target leaf sequence of the multileaf collimator outputted by the preset model into the radiotherapy planning system, the radiotherapy planning system controls the linear accelerator to operate; and after the linear accelerator operates, operation is still performed by taking the target leaf sequence as the leaf sequence of the multileaf collimator in the linear accelerator to implement a radiotherapy plan.

In conclusion, in the method for controlling multileaf collimator in radiotherapy provided according to embodiments of the present disclosure, by acquiring a preset model; outputting regarding a radiotherapy target, a target leaf sequence of a multileaf collimator through the preset model, to obtain a planning file; and importing the planning file into a radiotherapy planning system to control a linear accelerator to operate, so as to implement a radiotherapy plan, the calculation and operation speed for calculating the leaf sequence of the multileaf collimator by using a pre-trained model is high, and the accuracy and stability of the leaf sequence can be improved, thereby shortening the treatment time of a patient, and reducing the workload of physicists in designing a radiotherapy plan, which further solves the technical problem in the related art of poor accuracy and stability in determining a leaf sequence of a multileaf collimator.

The described preset model is a pre-trained model, for example, sample data is acquired before acquiring a preset model, wherein the sample data comprises: fluence maps in historical planning files; and reinforcement learning and training is performed by means of a neural network model by using the sample data to generate the preset model. As reinforcement learning requires a large number of fluence maps to train a good result, the described fluence maps in historical planning files can be fluence maps in collected planning files of previous radiotherapy plans, and may also be simulated fluence maps in historical planning files.

In addition, before acquiring sample data, a control environment of the multileaf collimator needs to be set, i.e., the environment of a training frame. Optionally, the method further comprises: setting environmental parameters of the training frame according to a model of the linear accelerator, wherein the environmental parameters at least comprise: a width of each leaf, a movement range of each leaf, a movement speed of each leaf, and a total number of leaves of the multileaf collimator; setting states of leaves of the training frame, wherein the states at least comprise: a leaf position where a current leaf is located, a currently obtained fluence map, and a target fluence map; and setting a reward function for the leaves of the training frame, wherein the reward function is used for calculating a difference between the currently outputted fluence map and the target fluence map, and allocating a reward corresponding to the leaf position. That is, settings of the control environment of the multileaf collimator mainly comprise: basic settings, action settings, state setting and reward setting of the multileaf collimator.

The basic settings of the multileaf collimator comprise: flexibly adjusting the number of leaves, and the width and movement range of the leaves of the multileaf collimator according to the model of the linear accelerator, so that a network output corresponds to the machine model.

The action settings comprise: actions comprising a motion sequence of leaves of the multileaf collimator and weights of irradiation fields, and designing action parameters according to the machine model of the linear accelerator, such as the movable range and motion speed of each blade and the total number of leaves. In addition, normalized weights are divided into N equal parts, and each level serves as an independent action parameter.

The state setting comprises: in reinforcement learning, the current state inputted to the network each time needs to be provided. The set state comprises a total of several channels, which respectively represent the position of the current leaf and the weight of an irradiation field, the historical positions of leaves and the weights of irradiation fields, and the target fluence map, etc. These channels are connected in series and then enter a neural network of reinforcement learning to obtain an output action, and the action is then fed back to the state, so that the state changes again.

The reward setting comprises: calculating a distribution difference between the currently outputted fluence map (obtained through calculation according to the weight distribution of accumulated irradiation fields) and the target fluence map, and allocating a reward corresponding to the specific leaf position. Optimizing this reward function can make a final result tend to the target fluence map.

Optionally, the simulated state of the multileaf collimator in the environment of the training frame is determined according to the environmental parameters, the states and the reward function.

Then, performing reinforcement learning and training on the sample data and the simulated state of the multileaf collimator by a first network of the neural network model to obtain a simulated leaf sequence of the multileaf collimator, wherein the simulated leaf sequence of the multileaf collimator comprises: coordinate positions of the leaves and weights of irradiation fields; evaluating the simulated leaf sequence of the multileaf collimator by a second network in the neural network model; and adjusting parameters in the first network and the second network of the neural network model according to an evaluation result to generate the preset model.

For example, in some embodiments of the present disclosure, a deep reinforcement learning algorithm architecture is used, the first network may be an Actor network, and the second network is a Critic network. The sample data and the state of the multileaf collimator are inputted into the Actor network, and the Actor network outputs a leaf sequence (comprising a dimension of the movement range of leaves and a dimension of weights of irradiation fields). Then, a simulation environment changes a current fluence map according to the leaf sequence, and the Critic network evaluates according to the changed fluence map and the target fluence map. This evaluation can enable the first network to adjust network parameters according to the evaluation, and can also enable network parameters of the second network to be adjusted; and then a difference between the current fluence map and the target fluence map is calculated, the difference is compared with the obtained evaluation above, and parameters of the second network are adjusted according to the comparison. The described preset model is generated by multiple iterations, thereby ensuring the accuracy and stability of a leaf sequence of a multileaf collimator outputted by the generated preset model.

Moreover, constraints of treatment time and leaf shapes are added in a model training process, and the leaf sequence is comprehensively optimized, wherein the treatment time is determined by both the leaf speed and motion amplitude of the leaf sequence, the leaf speed is determined when the environment is initialized, and the motion amplitude of the leaf sequence is obtained by calculating according to a sequence outputted by the network. The treatment time of a patient is shortened.

Optionally, after importing the planning file into a radiotherapy planning system to control a linear accelerator to operate so as to implement a radiotherapy plan, the method further comprises: importing the planning file into the radiotherapy planning system to control the linear accelerator to operate to acquire an actual fluence map; and evaluating the preset model based on the actual fluence map and the target fluence map.

In the described solution, the planning file is imported into the radiotherapy planning system to control the linear accelerator to operate to acquire an actual fluence map; and the preset model is evaluated based on the actual fluence map and the target fluence map, and the performance and precision of the described preset model can be evaluated. Alternatively, after a reinforcement learning model is trained, an actual radiotherapy planning system can be used for evaluation. First, the radiotherapy planning system generates a fluence map of each subfield according to a loss function provided by a doctor, the generated preset model generates a corresponding sequence of the multileaf collimator according to the fluence map, and writes the sequence of the multileaf collimator into a planning file, then the radiotherapy planning system is used to read the plan, and a dose volume histogram is generated by means of measurement calculation to verify whether the plan can pass the radiotherapy planning system. In addition, a fluence map is inversely calculated according to a sequence of the multileaf collimator obtained by the preset model, the fluence map is compared with the target fluence map, and a mean absolute error is used to calculate a difference of mean square errors to obtain a precision. The calculated precision can feed back a control result of the multileaf collimator, thereby improving the accuracy and stability of the leaf sequence, shortening the treatment time of a patient, and further reducing the workload of physicists in designing a radiotherapy plan, which further solves the technical problem in the related art of poor accuracy and stability in determining a leaf sequence of a multileaf collimator.

It should be noted that the steps illustrated in the flowchart of the drawings can be executed in a computer system having a set of computer-executable instructions, and although a logical order is shown in the flowchart, in some cases, the steps shown or described can be executed in a different order from that described here.

Embodiments of the present disclosure further provide an apparatus for controlling multileaf collimator in radiotherapy. It should be noted that the apparatus for controlling multileaf collimator in radiotherapy of the embodiments of the present disclosure can be used for executing the method for controlling multileaf collimator in radiotherapy provided in the embodiments of the present disclosure. Hereinafter, the apparatus for controlling multileaf collimator in radiotherapy provided in the embodiments of the present disclosure is introduced.

Figure 2:
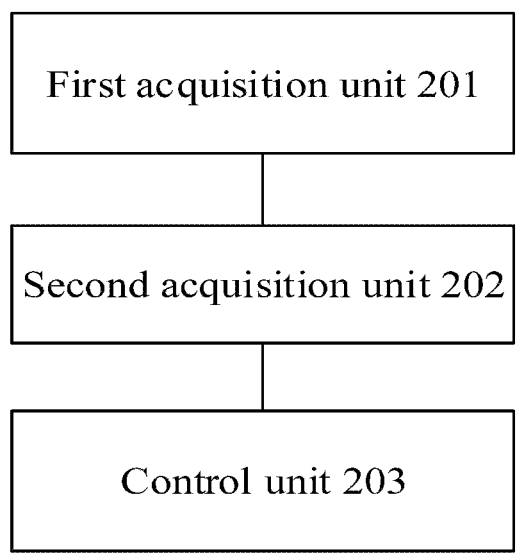
FIG. 2 is a schematic diagram of an apparatus for controlling multileaf collimator in radiotherapy provided according to embodiments of the present disclosure.

FIG. 2 is a schematic diagram of an apparatus for controlling multileaf collimator in radiotherapy provided according to embodiments of the present disclosure. As shown in FIG. 2, the apparatus comprises: a first acquisition unit 201, a second acquisition unit 202 and a control unit 203.

Specifically, the first acquisition unit 201 is configured to acquire a preset model;
the second acquisition unit 202 is configured to output, regarding a radiotherapy target, a target leaf sequence of a multileaf collimator through the preset model, to obtain a planning file, and
the control unit 203 is configured to import the planning file into a radiotherapy planning system to control a linear accelerator to operate, so as to implement a radiotherapy plan.

In conclusion, in the apparatus for controlling multileaf collimator in radiotherapy according to embodiments of the present disclosure, the first acquisition unit 201 acquires a preset model; the second acquisition unit 202 outputs, regarding a radiotherapy target, a target leaf sequence of a multileaf collimator through the preset model, to obtain a planning file; and the control unit 203 imports the planning file into a radiotherapy planning system to control a linear accelerator to operate so as to implement a radiotherapy plan, the calculation and operation speed for calculating the leaf sequence of the multileaf collimator by using a pretrained model is high, and the accuracy and stability of the leaf sequence can be improved, thereby shortening the treatment time of a patient, and reducing the workload of physicists in designing a radiotherapy plan, which further solves the technical problem in the related art of poor accuracy and stability in determining a leaf sequence of a multileaf collimator.

Optionally, in the apparatus for controlling multileaf collimator in radiotherapy provided in the embodiments of the present disclosure, the apparatus further comprising: a third acquisition unit, which is configured to acquire sample data before acquiring a preset model, wherein the sample data comprises: fluence maps in historical planning files; and a generation unit, which is configured to perform reinforcement learning and training through a neural network model by using the sample data, to generate the preset model.

Optionally, in the apparatus for controlling multileaf collimator in radiotherapy provided in the embodiments of the present disclosure, the apparatus further comprises: a first setting unit, which is configured to set environmental parameters of a training frame according to a model of the linear accelerator before acquiring sample data, wherein the environmental parameters at least comprise: a width of each leaf, a movement range of each leaf, a movement speed of each leaf, and a total number of leaves of the multileaf collimator; a second setting unit, which is configured to set states of leaves of the training frame, wherein the states at least comprise: a leaf position where a current leaf is located, a currently obtained fluence map, and a target fluence map; and a third setting unit, which is configured to set a reward function for the leaves of the training frame, wherein the reward function is used for calculating a difference between the currently outputted fluence map and the target fluence map, and configured to allocate a reward corresponding to the leaf position.

Optionally, in the apparatus for controlling multileaf collimator in radiotherapy provided in the embodiments of the present disclosure, the apparatus further comprises: a first determination unit, which is configured to determine a simulated state of the multileaf collimator in an environment according to the environmental parameters, the states and the reward function before acquiring sample data.

Optionally, in the apparatus for controlling multileaf collimator in radiotherapy provided in the embodiments of the present disclosure, the first determination unit comprises: an acquisition module, which is configured to perform reinforcement learning and training on the sample data and the simulated state of the multileaf collimator by a first network of the neural network model to obtain a simulated leaf sequence of the multileaf collimator, wherein the simulated leaf sequence of the multileaf collimator comprises: coordinate positions of the leaves and weights of irradiation fields; an evaluation module, which is configured to evaluate the simulated leaf sequence of the multileaf collimator by a second network in the neural network model; and an adjustment module, which is configured to adjust parameters in the first network and the second network of the neural network model according to an evaluation result, to generate the preset model.

Optionally, in the apparatus for controlling multileaf collimator in radiotherapy provided in the embodiments of the present disclosure, the apparatus further comprises: a fourth acquisition unit, which is configured to import, after importing the planning file into a radiotherapy planning system to control a linear accelerator to operate to implement a radiotherapy plan, the planning file into the radiotherapy planning system to control the linear accelerator to operate to acquire an actual fluence map; and an evaluation unit, which is configured to evaluate the preset model based on the actual fluence map and the target fluence map.

A graphic transformation apparatus comprises a processor and a memory; the first acquisition unit 201, the second acquisition unit 202 and the control unit 203, etc. are all stored in the memory as program units, and the processor executes the described program units stored in the memory to implement corresponding functions.

The processor comprises a kernel, and the kernel retrieves corresponding program units in the memory. One or more kernels can be provided, and by adjusting parameters of the kernels, the accuracy and stability of the leaf sequence can be improved, thereby shortening the treatment time of a patient, and reducing the workload of physicists in designing a radiotherapy plan.

The memory may comprise forms such as a non-permanent memory, a random access memory (RAM), and/or a non-transitory memory such as a read-only memory (ROM) or a flash RAM, in a computer-readable medium. The memory comprises at least one memory chip.

Embodiments of the present disclosure provide a non-transitory storage medium, on which a program is stored, and the program, when executed by the processor, implements the method for controlling multileaf collimator in radiotherapy.

Embodiments of the present disclosure provide a processor, the processor is used for running a program, wherein when the program is running, the method for controlling multileaf collimator in radiotherapy is implemented.

Embodiments of the present disclosure provide an electronic apparatus, comprising a processor and a memory; computer-readable instructions are stored in the memory, and the processor is configured to run the computer-readable instructions, wherein when the computer-readable instructions are running, the method for controlling multileaf collimator in radiotherapy according to any one of the above is implemented.

Embodiments of the present disclosure provide a device, the device comprising a processor, a memory and a program which is stored in the memory and can be run on the processor, wherein when the processor executes the program, the following steps are achieved: acquiring a preset model; outputting, regarding a radiotherapy target, a target leaf sequence of a multileaf collimator through the preset model, to obtain a planning file; and importing the planning file into a radiotherapy planning system to control a linear accelerator to operate, so as to implement a radiotherapy plan.

The following steps can also be implemented when the processor executes the program: before acquiring a preset model, the method further comprises: acquiring sample data, wherein the sample data comprises: fluence maps in historical planning files; and performing reinforcement learning and training through a neural network model by using the sample data, to generate the preset model.

The following steps can also be implemented when the processor executes the program: before acquiring sample data, the method further comprises: setting environmental parameters of a training frame according to a model of the linear accelerator, wherein the environmental parameters at least comprise: a width of each leaf, a movement range of each leaf, a movement speed of each leaf, and a total number of leaves of the multileaf collimator; setting states of leaves of the training frame, wherein the states at least comprise: a leaf position where a current leaf is located, a currently obtained fluence map, and a target fluence map; and setting a reward function for the leaves of the training frame, wherein the reward function is used for calculating a difference between the currently outputted fluence map and the target fluence map, and allocating a reward corresponding to the leaf position.

The following steps can also be implemented when the processor executes the program: before acquiring sample data, the method further comprises: determining a simulated state of the multileaf collimator in an environment according to the environmental parameters, the states and the reward function.

The following steps can also be implemented when the processor executes the program: performing reinforcement learning and training through a neural network model by using the sample data to generate the preset model, comprises: performing reinforcement learning and training on the sample data and the simulated state of the multileaf collimator by a first network of the neural network model to obtain a simulated leaf sequence of the multileaf collimator, wherein the simulated leaf sequence of the multileaf collimator comprises: coordinate positions of the leaves and weights of irradiation fields; evaluating the simulated leaf sequence of the multileaf collimator by a second network in the neural network model; and adjusting parameters in the first network and the second network of the neural network model according to an evaluation result, to generate the preset model.

The following steps can also be implemented when the processor executes the program: after importing the planning file into a radiotherapy planning system to control a linear accelerator to operate so as to implement a radiotherapy plan, the method further comprises: importing the planning file into the radiotherapy planning system to control the linear accelerator to operate to acquire an actual fluence map; and evaluating the preset model based on the actual fluence map and the target fluence map.

As will be appreciated by a person skilled in the art, embodiments of the present disclosure may be provided as a method, a system, or a computer program product. Therefore, the present disclosure may take the form of entire hardware embodiments, entire software embodiments or embodiments combining software and hardware. Furthermore, the present disclosure may take the form of a computer program product implemented on one or more computer-executable storage media (including but not limited to a disk memory, a CD-ROM, an optical memory, etc.) containing computer-executable program codes.

Some embodiments of the present disclosure are described with reference to the flowcharts and/or block diagrams of the method, device (system), and computer program product according to the embodiments of the present disclosure. It should be understood that computer program instructions may be used to implement each process and/or block in the flowchart and/or block diagram and a combination of processes and/or blocks in the flowchart and/or the block diagram. These computer program instructions may be provided to a processor of a general-purpose computer, a special-purpose computer, an embedded processor or other programmable data processing devices to produce a machine, such that an apparatus for implementing functions specified in one or more processes in the flowchart and/or one or more blocks in the block diagram is generated by executing the instructions by the processor of the computer or other programmable data processing devices.

These computer program instructions can also be stored in a computer-readable memory that can direct a computer or other programmable data processing devices to operate in a particular manner, such that the instructions stored in the computer-readable memory produce a product comprising an instruction device, the instruction device implementing functions specified in one or more processes of the flowchart and/or one or more blocks of the block diagram.

These computer program instructions may also be loaded onto a computer or other programmable data processing devices, so that a series of operation steps are executed on the computer or other programmable data processing devices to generate processing implemented by the computer, so that the instructions executed on the computer or other programmable data processing devices provide steps for implementing functions specified in one or more processes in the flowchart and/or one or more blocks in the block diagram.

In a typical configuration, a computing device comprises one or more processors (CPUs), an input/output interface, a network interface, and a memory.

The memory may comprise forms such as a non-permanent memory, a random access memory (RAM), and/or a non-transitory memory such as a read-only memory (ROM) or a flash RAM, in a computer-readable medium. The memory is an example of a computer-readable medium.

The computer-readable medium, comprising both permanent and non-permanent, and removable and non-removable medium, may achieve information storage by any method or technology. The information may be computer-readable instructions, data structures, modules of a program, or other data. Examples of the computer storage medium comprise but are not limited to, phase change memory (PRAM), static random-access memory (SRAM), dynamic random-access memory (DRAM), other types of random-access memories (RAM), read-only memory (ROM), electrically erasable programmable read-only memory (EEPROM), flash memory or other memory technology, compact disc read-only memory (CD-ROM), digital versatile disc (DVD) or other optical storage, magnetic cassettes, magnetic tape magnetic disk storage or other magnetic storage devices, or any other non-transmission media, which may be used to store information that may be accessed by the computing device. As defined herein, the computer-readable media do not comprise transitory computer-readable media, such as modulated data signals and carriers.

It should also be noted that the terms "comprise", "comprises", or any other variations thereof are intended to cover a non-exclusive inclusion, so that a process, a method, a commodity, or a device that comprises a series of elements not only comprises those elements, but also comprises other elements that are not explicitly listed, or further comprises inherent elements of the process, the method, the commodity, or the device. Without further limitation, an element defined by a sentence "comprise a . . . " does not exclude other same elements existing in a process, a method, a commodity, or a device that comprises the element.

As will be appreciated by one skilled in the art, embodiments of the present disclosure may be provided as a method, a system, or a computer program product. Therefore, the present disclosure may take the form of entire hardware embodiments, entire software embodiments or embodiments combining software and hardware. Furthermore, the present disclosure may take the form of a computer program product implemented on one or more computer-executable storage media (including but not limited to a disk memory, a CD-ROM, an optical memory, etc.) containing computer-executable program codes.

The described content merely relates to embodiments of the present disclosure, and is not intended to limit some embodiments of the present disclosure. For those skilled in the art, the present disclosure may have various modifications and variations. Any modifications, equivalent replacements, improvements, etc. made within the spirit and principle of the present disclosure shall fall within the scope of the claims of the present disclosure.

The invention claimed is:

1. A method for controlling multileaf collimator in radiotherapy, comprising:
   acquiring a preset model;
   outputting, regarding a radiotherapy target, a target leaf sequence of a multileaf collimator through the preset model, to obtain a planning file; and
   importing the planning file into a radiotherapy planning system to control a linear accelerator to operate, so as to implement a radiotherapy plan;
   wherein before acquiring a preset model, the method further comprises:
   acquiring sample data, wherein the sample data comprises: fluence maps in historical planning files; and
   performing reinforcement learning and training through a neural network model by using the sample data, to generate the preset model.

2. The method as claimed in claim 1, wherein before acquiring sample data, the method further comprises:
   setting environmental parameters of a training frame according to a model of the linear accelerator, wherein the environmental parameters at least comprise: a width of each leaf, a movement range of each leaf, a movement speed of each leaf, and a total number of leaves of the multileaf collimator;
   setting states of leaves of the training frame, wherein the states at least comprise: a leaf position where a current leaf is located, a currently obtained fluence map, and a target fluence map; and
   setting a reward function for the leaves of the training frame, wherein the reward function is used for calculating a difference between the currently outputted fluence map and the target fluence map, and allocating a reward corresponding to the leaf position.

3. The method as claimed in claim 2, wherein before acquiring sample data, the method further comprises:
   determining a simulated state of the multileaf collimator in an environment according to the environmental parameters, the states and the reward function.

4. The method as claimed in claim 3, wherein performing reinforcement learning and training through a neural network model by using the sample data to generate the preset model, comprises:
   performing reinforcement learning and training on the sample data and the simulated state of the multileaf collimator by a first network of the neural network model to obtain a simulated leaf sequence of the multileaf collimator, wherein the simulated leaf sequence of the multileaf collimator comprises: coordinate positions of the leaves and weights of irradiation fields;

evaluating the simulated leaf sequence of the multileaf collimator by a second network in the neural network model; and adjusting parameters in the first network and the second network of the neural network model according to an evaluation result to generate the preset model.

5. The method as claimed in claim 1, wherein after importing the planning file into a radiotherapy planning system to control a linear accelerator to operate, so as to implement a radiotherapy plan, the method further comprises:

importing the planning file into the radiotherapy planning system to control the linear accelerator to operate, to acquire an actual fluence map; and evaluating the preset model based on the actual fluence map and the target fluence map.

6. A non-transitory storage medium, wherein the non-transitory storage medium comprises a program stored therein, wherein when the program runs, a device where the non-transitory storage medium is located is controlled to perform the method as claimed in claim 1.

7. An electronic apparatus, comprising a processor and a memory; wherein computer-readable instructions are stored in the memory, and the processor is configured to run the computer-readable instructions, wherein when the computer-readable instructions are running, the method as claimed in claim 1 is implemented.

8. An apparatus for controlling multileaf collimator in radiotherapy, comprising:

a first acquisition unit, which is configured to acquire a preset model;

a second acquisition unit, which is configured to output, regarding a radiotherapy target, a target leaf sequence of a multileaf collimator through the preset model, to obtain a planning file; and a control unit, which is configured to import the planning file into a radiotherapy planning system to control a linear accelerator to operate, so as to implement a radiotherapy plan;

wherein the apparatus further comprises:

a third acquisition unit, which is configured to acquire sample data before acquiring a preset model, wherein the sample data comprises: fluence maps in historical planning files; and a generation unit, which is configured to perform reinforcement learning and training through a neural network model by using the sample data, to generate the preset model.

* * * * *